United States Patent [19]

Doerr et al.

[11] Patent Number: 4,461,553

[45] Date of Patent: Jul. 24, 1984

[54] DYNAMIC HEAD MOTION MEASURING SYSTEM

[75] Inventors: Joseph E. Doerr, Albuquerque, N. Mex.; Tomas J. Bozack, Ridgecrest, Calif.

[73] Assignee: The United States of America as represented by the Secretary of the Navy, Washington, D.C.

[21] Appl. No.: 389,807

[22] Filed: Jun. 18, 1982

[51] Int. Cl.³ .................. G03B 19/18; G03B 21/32
[52] U.S. Cl. ........................................ 352/39; 352/57
[58] Field of Search .................. 352/39, 57; 356/390

[56] References Cited

U.S. PATENT DOCUMENTS

| | | | |
|---|---|---|---|
| 1,470,407 | 10/1923 | Watson | 352/39 |
| 2,565,381 | 8/1951 | Leighton | 33/221 |
| 3,074,170 | 1/1963 | Zabel et al. | 33/1 |
| 3,121,322 | 2/1964 | Caldwell | 352/57 |
| 3,353,282 | 11/1967 | Sneed | 35/29 |
| 3,694,072 | 9/1972 | Danko et al. | 352/57 |
| 3,699,856 | 10/1972 | Chabot et al. | 95/1.1 |
| 4,197,855 | 4/1980 | Lewin | 128/653 |

*Primary Examiner*—Monroe H. Hayes
*Attorney, Agent, or Firm*—Robert F. Beers; W. Thom Skeer

[57] ABSTRACT

A stereo photographic measurement system having two wide angle lenses connected to a high speed motion picture camera by fiber-optic imaging bundles, and a target system, the camera and lenses being mounted upon one object and the target being mounted upon another object subject to motion relative thereto within the overlapping views of the lenses. In one embodiment head motion relative to the subject's torso during parachute opening is measured by this system with the target mounted on the back of the head and the lenses mounted near the base of the neck. Measurements of target position in each frame of stereo film by comparison of position of squares on the target are used to calculate head motion with respect to the upper torso.

8 Claims, 4 Drawing Figures

DYNAMIC HEAD MOTION MEASURING SYSTEM

BACKGROUND OF THE INVENTION

1. Field of the Invention

This invention pertains to the field of measuring systems. More particularly, this invention pertains to systems for measurement of relative motions. Still more particularly, but without limitation thereto, this invention pertains to systems for measurement of head movement of a person relative to their trunk when the person is exposed to sudden accelerations.

2. Description of the Prior Art

Prior attempts to measure relative head motion of a subject during sudden accelerations such as during parachute opening have employed accelerometers. The accelerometers were attached to a subject using a custom formed metal bite plate held in place with a series of straps around the head. A custom molded plastic device placed on the subject's back over the first thoracic vertebra, and held in place with straps around the subject's torso, was used as a torso accelerometer mount. When this system was adapted to gather head motion data during parachute opening tests, the resulting data was difficult to analyze due to uncertainty in initial conditions and cumulative errors resulting from the integration of acceleration data. Also, the safety of the mouth mount in the parachute test environment came into question as a result of instances of chipped teeth apparently resulting from objects hitting the mount assembly.

SUMMARY OF THE INVENTION

It is an object of this invention to provide a system for measurement of relative motion capable of providing accurate initial position data.

It is a further object of this invention to provide a system for measurement of head motion of a person relative to his torso when subjected to sudden accelerations such as in parachute opening tests which is safe for the subject.

These objects and others have been demonstrated by the present invention which comprises a stereo photographic measurement system having two wide angle lenses connected to a high speed motion picture camera by fiber-optic imaging bundles, and a target system, the camera and lenses being mounted upon one object and the target being mounted upon another object subject to motion relative thereto.

In the embodiment wherein a person is subjected to parachute opening tests, the camera is located on the chest with fiber-optic light guide bundles leading to lenses mounted near the base of the neck, and the target is mounted on the lower rear portion of a custom fitted helmet worn by the test person. Head motion relative to the subject's torso during parachute opening is measured by this system. The target comprises a pattern of checkerboard squares, and displacement of the target will move the squares relative to the camera lenses and ultimately the frame of film exposed in the camera. Measurements of the position of the photo target in each frame of stereo film by means of the target squares on the target are used to calculate the three-dimensional motion of the head with respect to the upper torso.

DESCRIPTION OF THE PREFERRED EMBODIMENT

Figure 1:
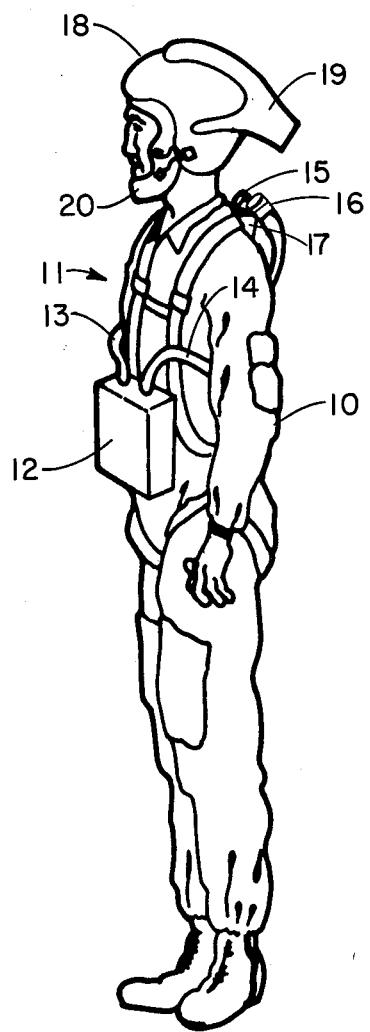
FIG. 1 is an elevation view of a test subject wearing the test equipment of the invention.

Referring to FIG. 1, subject 10 is wearing the inventive motion detection system 11. Detection system 11 comprises high speed 16 mm stereo motion picture camera 12 which operates at 200 frames per second. Fiber-optic light guide bundles 13, 14 connect and transfer images between wide angle lenses 15, 16 and camera 12. Lenses 15 and 16 are attached to mount 17 which is centrally located on the upper back of the subject 10. Custom fitted helmet 18 is worn on the head of subject 10. Target 19 is mounted on the lower posterior portion of helmet 18. A face plate 20 strapped to helmet 18 retains helmet 18 in an immobile position of the head of the subject 10.

Figure 2:
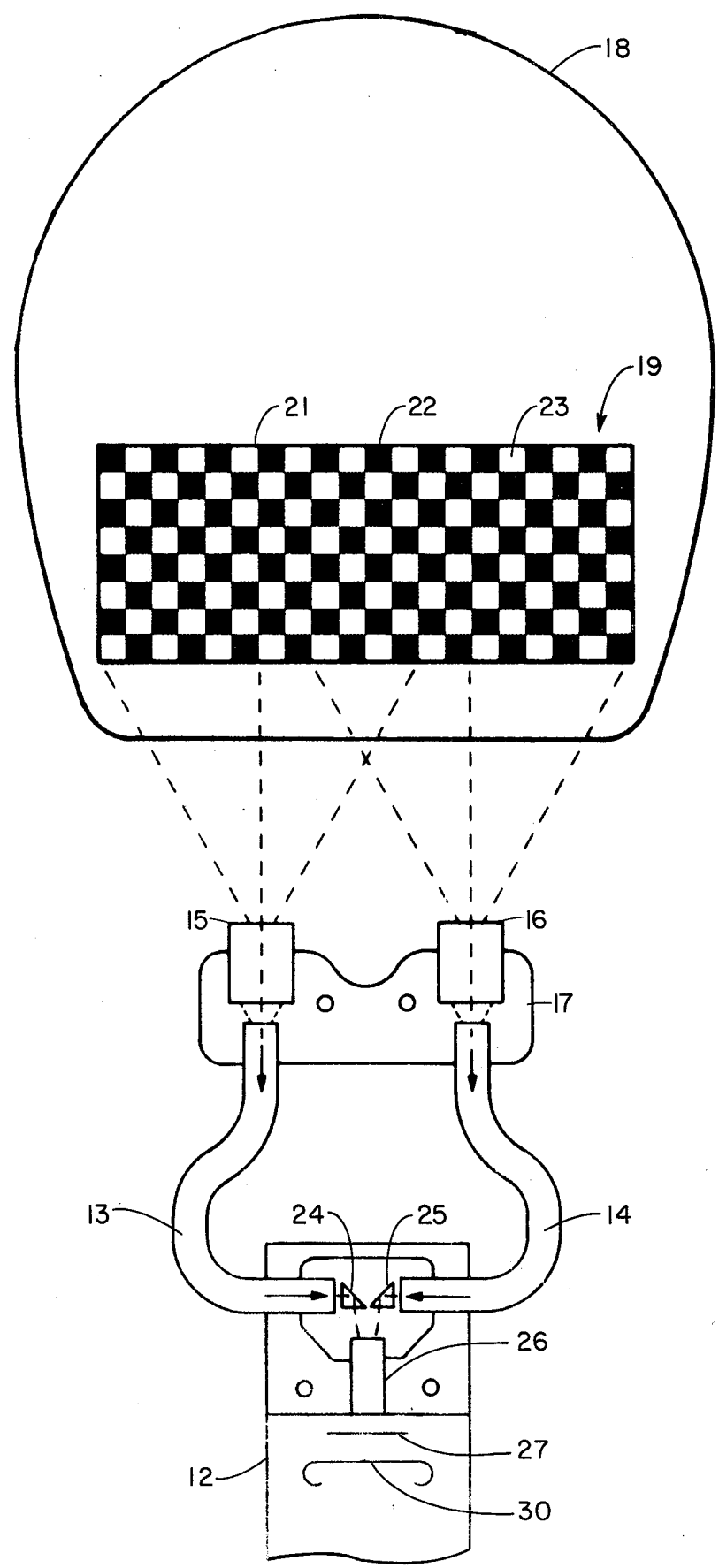
FIG. 2 is a schematic view showing a rear view of the target, lenses, and lens mount of the invention as worn by a test subject and a diagrammatic view of the camera the invention with connecting fiber optic light guide bundles.

Referring to FIG. 2, the target 19 bears a checkerboard pattern 21 having alternating black squares 22 and white squares 23. FIG. 2 shows the positional relationship between the lenses 15 and 16 as mounted on mount 17 and directed toward target 19 on helmet 18. Fiber optic light guide bundles 13 and 14 are mounted on mount 17 so as to receive images from corresponding wide angle lenses 15 and 16 and convey those images to camera 12. In camera 12 the images from fiber optic light guide bundles 13 and 14 are directed by corresponding prisms 24 and 25 to camera lens 26 which focuses the images through shutter 27 to film 30.

Figure 3:
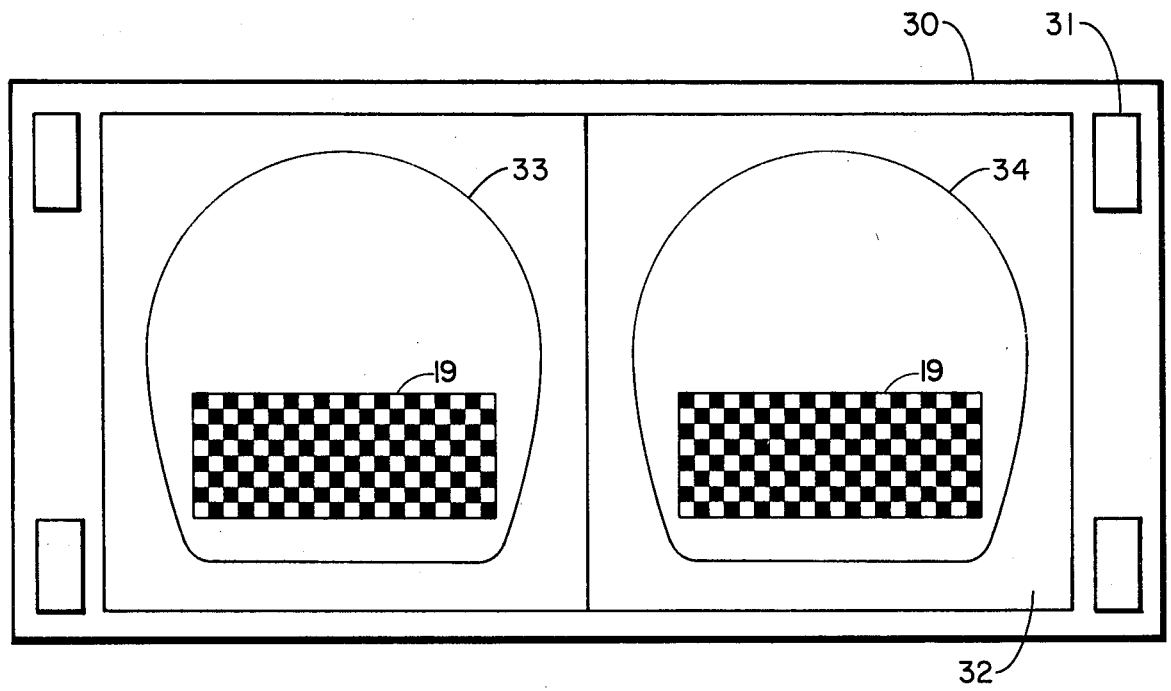
FIG. 3 is a view of a typical exposed stereo film frame obtained according to the practice of the invention.

Referring to FIG. 3 16 mm motion picture film 30 having sprocket holes 31 is illustrated with an exposed frame 32 having two images 33 and 34. The target in the two images records, according to the geometry of the system, the spatial position of the target 19 at the time of frame exposure as further discussed below.

In operation, stereo lenses 15 and 16 transmit images through fiber-optical light guide bundles 13, 14 to stereo motion picture camera 12. Camera 12 is operated at 200 frames per second. When relative motion between target 19 and lenses 15 and 16 occur, such as when the test subject is subjected to sudden accelerations, i.e. the subject's parachute opens, the images 31 and 32 on frames 33 of film 30 change accordingly. Specific positions of the target 19 at particular instants of time can be determined by analysis of a stereo frame 33. Since the frame rate of the camera is known, the time it takes for the target to move from one position to another can be determined by counting the number of frames between each relative position. Such data can be analyzed to determine head position, speed, and acceleration during movement. An initial time and frame can be established such as when the subject's parachute begins opening. From this data a complete measurement and description of head motion during the opening sequence can be made.

The camera 12 is a high speed 16 mm stereo motion picture camera operating at up to 200 frames per second, for example, model IVN Actionmaster/200 manufactured by Photo-Sonics, Inc. of Burbank, CA. Weight of the camera is 680 grams and the loaded 65-foot film magazine weighs 567 grams. Two light emitting diodes, one on each side of the film outside the picture area, provide a timing reference. A standard "C" mount couples the camera with the fiber-optic imaging system. A small bracket support houses the relay lens for additional strength at the "C" mount to endure shock forces during parachute opening. Power is supplied for the camera and data recording system by a 28 Volt dc, 4 amp rechargeable Nicad battery.

The fiber-optic imaging system comprises a pair of lenses, 15, 16 for example 4.5 mm F1.2 fish eye lenses aimed and focused to view the target system 19. The lenses 15, 16 are attached to a pair of fiber-optic imaging bundles, for example, each being approximately 8 mm in diameter and 914 mm long, carrying the image to the high speed camera 12.

Figure 4:
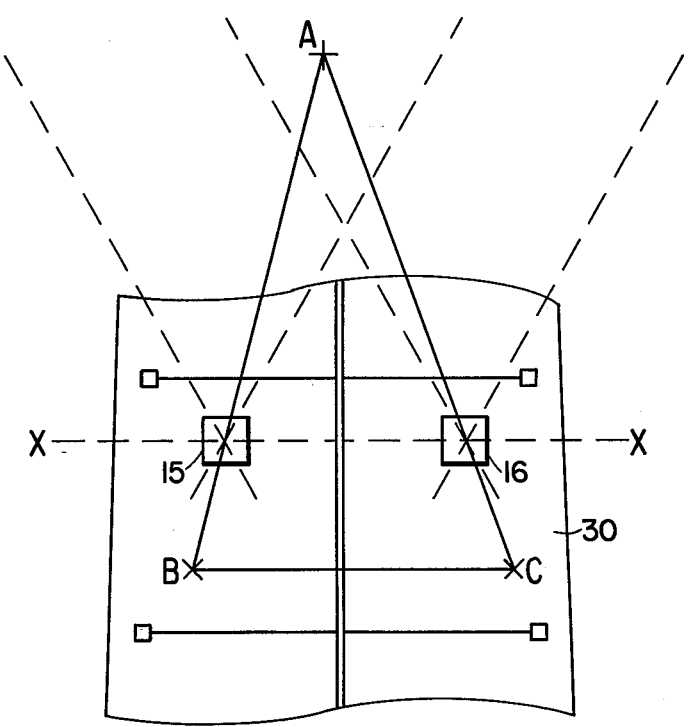
FIG. 4 is a diagram illustrating stereo measurement geometry.

Referring to FIG. 4, the position of a target point A can be determined geometrically. Each lens 15, 16 on the mount records an image on film 30 from its own point of view. Triangle ABC must have its sides AB and AC pass through each lens 15, 16 as shown. Therefore, the farther A is away from a line X, $X^1$ through the lenses, the shorter the length of line BC. Conversely, if A is closer to X, $X^1$ then BC becomes longer. As long as the triangle sides pivot at the lenses, it may be seen that points B and C will move in predictable and measureable directions and distances.

The invention configuration can be modified as desired such as providing a 90 degree twist in each fiber optic light guide bundle, which results in image pairs being positioned lengthwise of the exposed film rather than across the film as in FIG. 3. Also, the common field of view of the lenses can be increased by rotating the lenses inward toward each other by about 15 degrees respectively from parrllel so as to increase the overlapping of the fields of view.

Obviously many modifications and variations of the present invention are possible in the light of the above teachings. It is therefore to be understood that within the scope of the appended claims the invention may be practiced otherwise than specifically described.

We claim:

1. A dynamic measuring system for the measurement of head motions of a person comprising:
    A. A high speed camera having film, said camera for mounting upon the trunk of said person;
    B. A form fitted helmet to be worn on the head of said person;
    C. A target system mounted upon said helmet;
    D. A pair of fiber-optic light guides connected to said camera and aligned on said target system from differing angles; and
    E. A pair of lenses connected to said fiber optic light guides to triangulate the target system, whereby triangulation permits a frame by frame measurement of head movement.

2. The measuring system of claim 1 wherein said target is mounted upon the rear portion of said helmet.

3. The measuring system of claim 1 wherein said target system comprises at least one surface having an alternating dark and light checkerboard pattern.

4. The measurement system of claim 1 wherein said pair of fiber-optic light guides are aligned on said target by means of a mount attached to the base of the neck of said person.

5. The measurement system of claim 1 wherein said camera is mounted upon the chest of said person.

6. The measurement system of claim 1 wherein said camera is so configured and each frame of said film is exposed so that a pair of images of said target are formed upon said film.

7. The measurement system of claim 6 wherein said film defines sprocket holes uniformly distributed along the length of said film such that the rate of head movement can be determined by relating target displacement between pairs of frames to the sprocket holes traversed between those pairs of frames.

8. The measurement system of claim 7 further comprising at least one light emitting diode so arranged within said camera that a light flash emitted therefrom upon initiation of head motion at a given time zero will mark said film within said camera thus determining time zero with relation to said sprocket holes.

* * * * *